(12) United States Patent
Naito

(10) Patent No.: US 9,677,599 B2
(45) Date of Patent: Jun. 13, 2017

(54) INSERTION BODY, INSERTION APPARATUS, ROTATION UNIT AND ROTATIVE FORCE TRANSMISSION UNIT

(71) Applicant: OLYMPUS CORPORATION, Tokyo (JP)

(72) Inventor: Kimihiko Naito, Kawasaki (JP)

(73) Assignee: OLYMPUS CORPORATION, Tokyo (JP)

( * ) Notice: Subject to any disclaimer, the term of this patent is extended or adjusted under 35 U.S.C. 154(b) by 52 days.

(21) Appl. No.: 14/230,672

(22) Filed: Mar. 31, 2014

(65) Prior Publication Data

US 2014/0296771 A1    Oct. 2, 2014

Related U.S. Application Data

(63) Continuation of application No. PCT/JP2013/072480, filed on Aug. 22, 2013.

(30) Foreign Application Priority Data

Aug. 31, 2012  (JP) .................................. 2012-191545

(51) Int. Cl.
*A61B 1/00* (2006.01)
*A61B 1/04* (2006.01)
(Continued)

(52) U.S. Cl.
CPC .............. *F16C 1/06* (2013.01); *A61B 1/0016* (2013.01); *A61B 1/00133* (2013.01);
(Continued)

(58) Field of Classification Search
CPC ... A61B 1/00135; A61B 1/0016; A61B 1/018; A61B 1/00156; A61B 17/068;
(Continued)

(56) References Cited

U.S. PATENT DOCUMENTS

2002/0058857 A1*  5/2002  Smith .................... A61B 1/015
                                                              600/153
2005/0038317 A1*  2/2005  Ratnakar ............ A61B 1/00105
                                                              600/156
(Continued)

FOREIGN PATENT DOCUMENTS

EP        2 901 912 A1    8/2015
JP        2005-319121 A  11/2005
(Continued)

OTHER PUBLICATIONS

International Search Report dated Nov. 19, 2013 issued in PCT/JP2013/072480.
(Continued)

*Primary Examiner* — Matthew J Kasztejna
*Assistant Examiner* — Aaron B Fairchild
(74) *Attorney, Agent, or Firm* — Scully, Scott, Murphy & Presser, P.C.

(57) ABSTRACT

An insertion body includes: a base arranged in the central axis; a rotating body provided on an outer periphery of the base and rotatable around the central axis; and a channel which includes a guide provided at the base such that the rotative force transmitting section is able to be guided between a first position in which the rotative force transmitting section in the longitudinal axis can be inclined from the central axis when the rotative force transmission unit is inserted from the outside to the inside and a second position in which the rotative force transmitting section in the longitudinal axis is parallel to the central axis and a rotative force can be transmitted to the rotating body from the rotative force transmitting section, and through which the rotative force transmission unit is inserted through the opening end and the guide.

17 Claims, 8 Drawing Sheets

(51) Int. Cl.
*A61M 31/00* (2006.01)
*F16C 1/06* (2006.01)
*A61M 25/01* (2006.01)
*G02B 23/24* (2006.01)
*A61B 1/018* (2006.01)
*F16C 1/08* (2006.01)
*A61B 17/16* (2006.01)
*A61B 1/12* (2006.01)

(52) U.S. Cl.
CPC ...... *A61B 1/00135* (2013.01); *A61B 1/00156* (2013.01); *A61B 1/018* (2013.01); *A61M 25/01* (2013.01); *G02B 23/2476* (2013.01); *A61B 1/121* (2013.01); *A61B 17/1631* (2013.01); *F16C 1/08* (2013.01)

(58) Field of Classification Search
CPC .............. A61B 17/072; A61B 17/1285; A61B 2017/07214; A61B 17/320758; A61B 17/1631; A61B 2017/2905; F16C 1/06; F16C 1/08; F16D 1/00; F16D 2001/102; G02B 23/24; Y10T 74/20456; Y10T 74/20462; Y10S 464/901; A61M 25/01
USPC ........... 600/114, 137, 153; 74/507; 433/112; 606/139, 142, 151, 153, 219; 604/95.01
See application file for complete search history.

(56) References Cited

U.S. PATENT DOCUMENTS

| | | | |
|---|---|---|---|
| 2005/0090709 | A1 | 4/2005 | Okada et al. |
| 2006/0089533 | A1* | 4/2006 | Ziegler .............. A61B 1/00156 600/114 |
| 2006/0270901 | A1* | 11/2006 | Bern .................... A61B 1/0016 600/114 |
| 2008/0287961 | A1 | 11/2008 | Miyamoto et al. |
| 2011/0319713 | A1 | 12/2011 | Frassica et al. |

FOREIGN PATENT DOCUMENTS

| | | | | |
|---|---|---|---|---|
| JP | 2007-185394 | A | | 7/2007 |
| JP | 2009-254554 | A | | 11/2009 |
| JP | 2010-227170 | A | | 10/2010 |
| JP | 2010227170 | A | * 10/2010 | .......... A61B 1/0008 |
| JP | 2011-517967 | A | | 6/2011 |
| JP | 2011-520563 | A | | 7/2011 |

OTHER PUBLICATIONS

English translation of International Preliminary Report on Patentability together with the Written Opinion, dated Mar. 12, 2015 received in related International Application No. PCT/JP2013/072480.

Extended Supplementary European Search Report dated Mar. 16, 2016 in related European Application No. 13 83 2396.9.

* cited by examiner

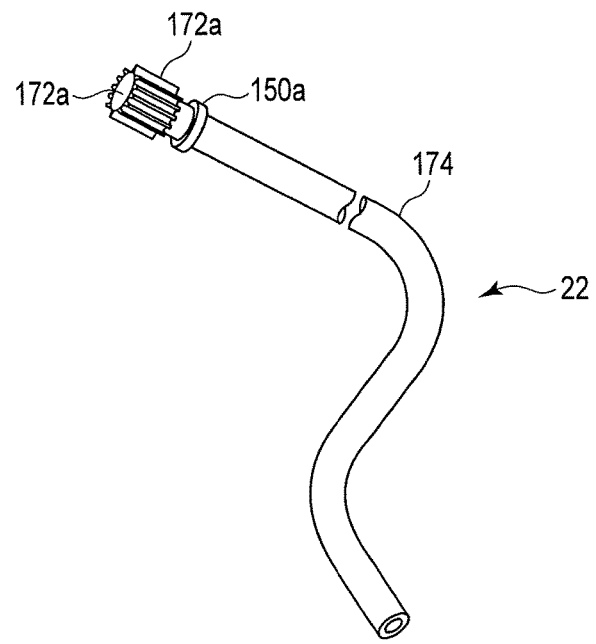
F I G. 2C
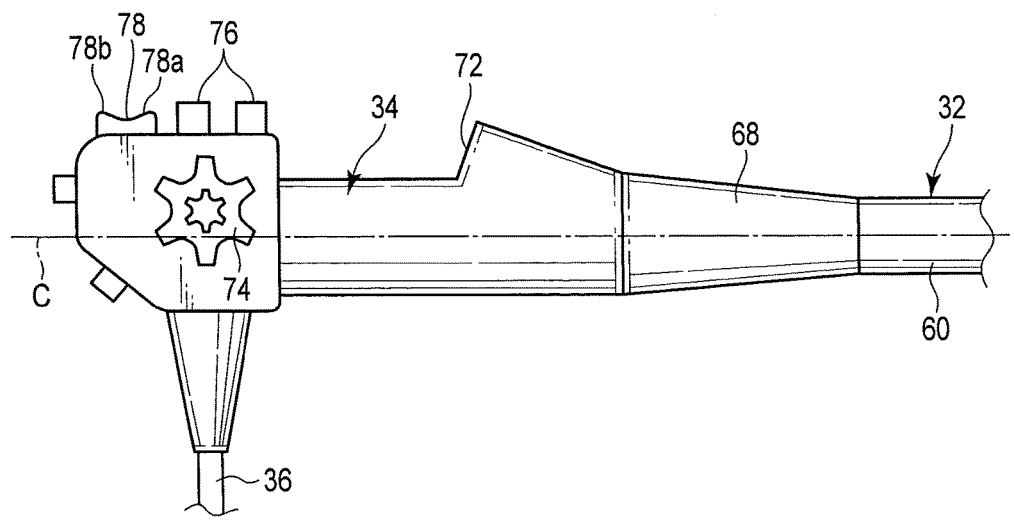
F I G. 3

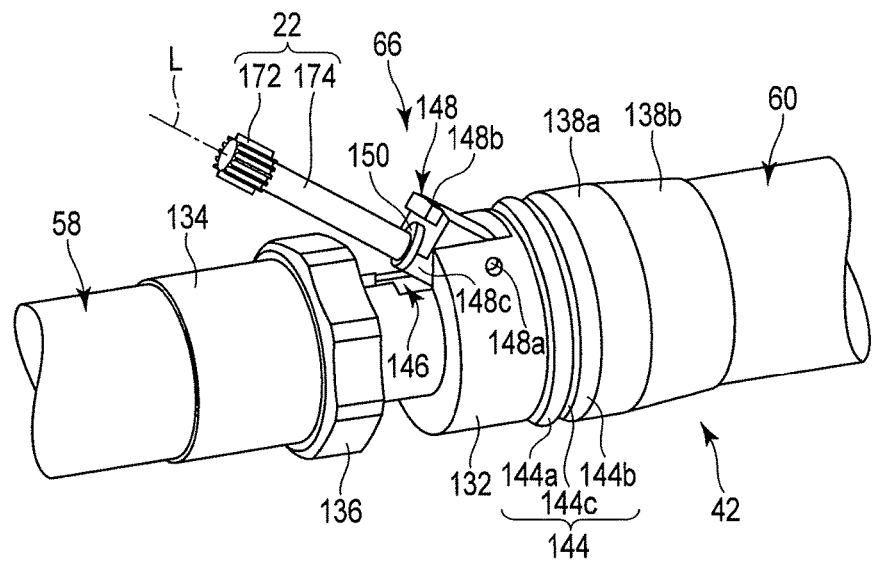
F I G. 5A
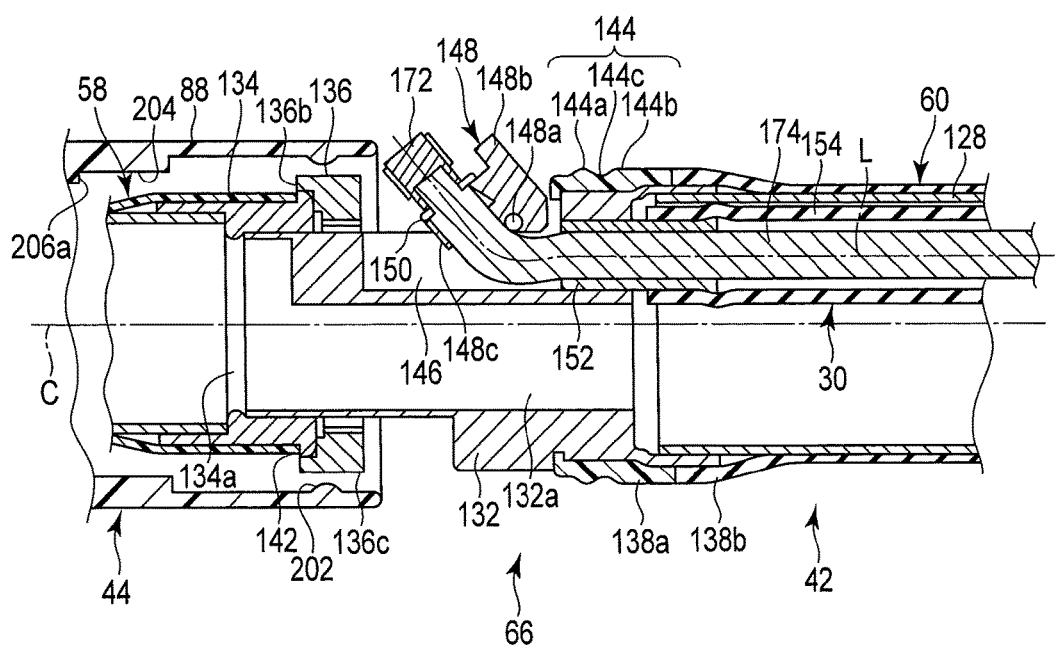
F I G. 5B

INSERTION BODY, INSERTION APPARATUS, ROTATION UNIT AND ROTATIVE FORCE TRANSMISSION UNIT

CROSS-REFERENCE TO RELATED APPLICATIONS

This application is a continuation application of PCT Application No. PCT/JP2013/072480, filed Aug. 22, 2013 and based upon and claiming the benefit of priority from prior Japanese Patent Application No. 2012-191545, filed Aug. 31, 2012, the entire contents of all of which are incorporated herein by reference.

BACKGROUND OF THE INVENTION

1. Field of the Invention

The present invention relates to an insertion apparatus and an insertion body that can be inserted into a narrow hole, and a rotation unit and a rotative force transmission unit that can be detachably attached to the insertion body.

2 Description of the Related Art

For example, an insertion section of an endoscope disclosed in Jpn. Pat. Appln. KOKAI Publication No. 2007-185394 includes a rotative force transmission unit including a rotation gear and a drive shaft fixed to a proximal end of the rotation gear. When a rotative force is transmitted to the rotation gear via the drive shaft of the rotative force transmission unit, a cylindrical spiral section including inner teeth engaged with the rotation gear rotates according to rotation of the rotation gear.

BRIEF SUMMARY OF THE INVENTION

One aspect of an elongated insertion body of an insertion apparatus in which a rotation unit rotatable around a central axis is provided on an external side of the insertion body, and into which a rotative force transmission unit including a rotative force transmitting section rotatable around a longitudinal axis different from the central axis and capable of transmitting a rotative force to the rotation unit is able to be inserted from an outside to an inside and removed from the inside to the outside of the insertion body according to the present invention, includes: a base arranged in the central axis; a rotating body provided on an outer periphery of the base and rotatable around the central axis; and a channel which includes a guide provided at the base such that the rotative force transmitting section is able to be guided between a first position in which the rotative force transmitting section in the longitudinal axis is able to be inclined from the central axis when the rotative force transmission unit is inserted from the outside to the inside or removed from the inside to the outside and a second position in which the rotative force transmitting section in the longitudinal axis is parallel to the central axis and a rotative force is able to be transmitted to the rotating body from the rotative force transmitting section, and an opening end provided at a distal end of the channel, and through which the rotative force transmission unit is inserted through the opening end and the guide.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2C is a schematic perspective view illustrating a modification example of the rotative force transmission unit that can be detachably attached to the endoscope of the endoscope system according to the embodiment.

FIG. 3 is a schematic view illustrating an operating section of the endoscope of the endoscope system according to the embodiment, viewed from the back side of FIG. 1.

FIG. 5A is a schematic perspective view illustrating a state in which a drive shaft of the rotative force transmission unit is introduced into a proximal end side of the insertion section from the flexible tube connector between the first flexible tube and the second flexible tube, in the insertion section of the endoscope of the endoscope system according to the embodiment.

FIG. 5B is a schematic vertical sectional view illustrating a state in which a drive shaft of the rotative force transmission unit is introduced into the proximal end side of the insertion section from the flexible tube connector between the first flexible tube and the second flexible tube, in the insertion section of the endoscope of the endoscope system according to the embodiment.

DETAILED DESCRIPTION OF THE INVENTION

Hereinafter, an embodiment for carrying out the present invention will be described with reference to FIGS. 1 to 8.

Figure 1:
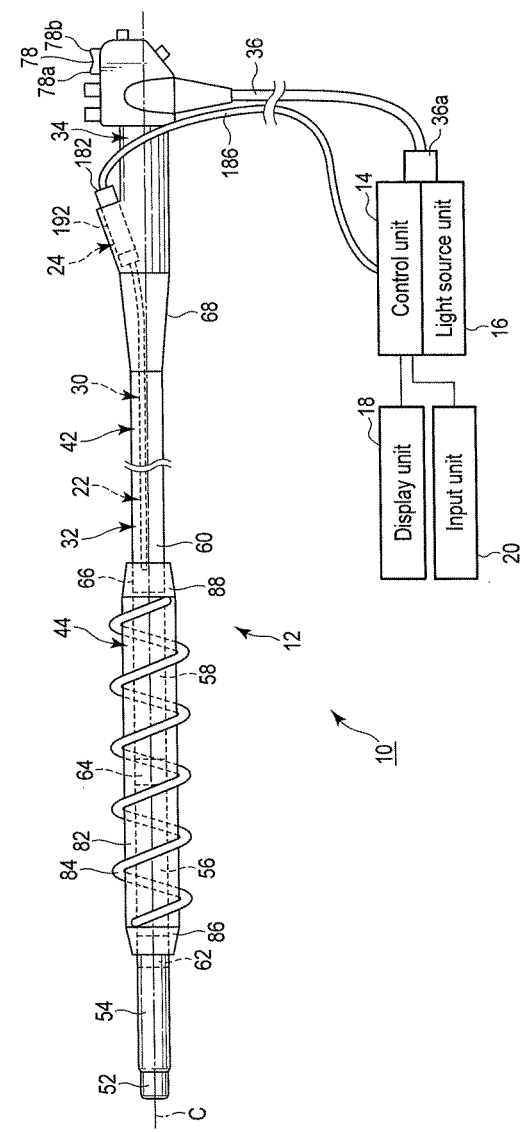
FIG. 1 is a schematic view illustrating an endoscope system according to an embodiment of the present invention.

As shown in FIG. 1, an endoscope system 10 of the present embodiment includes an endoscope (insertion apparatus) 12, a control unit 14 including an image processing unit such as an image processor, not shown, and configured to control the entire system 10, a light source unit 16, a display unit 18 such as a monitor, and an input unit 20 such as a keyboard and a mouse.

The light source unit 16 is electrically connected to the control unit 14. The display unit 18 and the input unit 20 are electrically connected to the control unit 14. The light source unit 16 may be omitted if a light source is provided at a distal-end rigid portion 52 of an insertion section 32, which will be described later, of the endoscope 12.

Figure 2A:
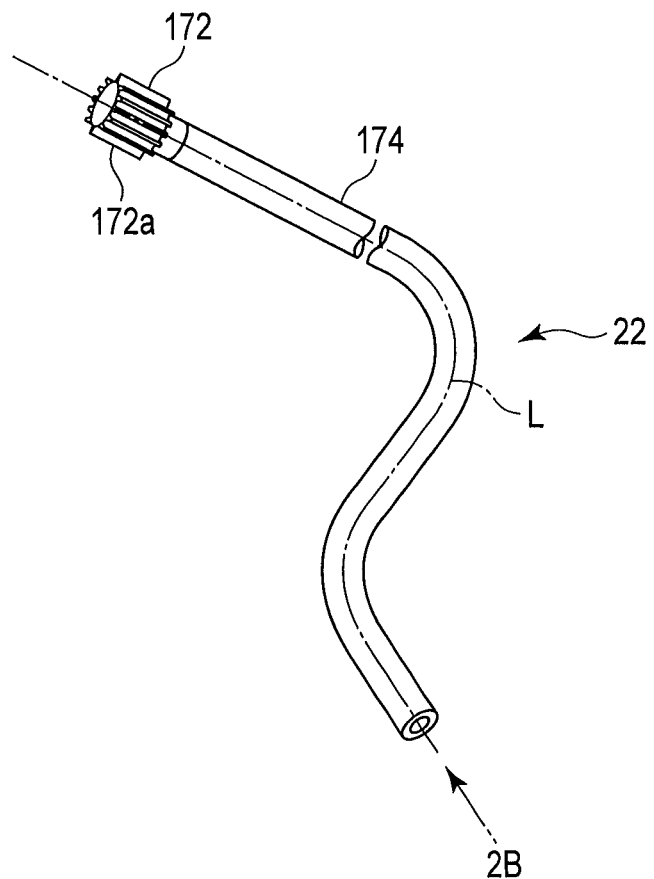
FIG. 2A is a schematic perspective view illustrating a rotative force transmission unit that can be detachably attached to an endoscope of the endoscope system according to the embodiment.

In the endoscope system 10 of the present embodiment, a rotative force transmission unit 22 shown in FIG. 2A and the driving source 24 shown in FIG. 1 can be detachably attached to the endoscope 12. That is, the endoscope 12 includes a channel 30 which defines an insertion path to and from which the rotative force transmission unit 22 and the driving source 24 are attached and detached.

The endoscope 12 includes an insertion section (insertion apparatus) 32 inserted into a narrow hole, such as the interior of a tube, and an operating section 34 provided on a proximal end of the insertion section 32. The insertion section 32 is inserted into lumina, such as the interior of the large intestine and the interior of the small intestine. One end of a universal cable 36 is connected to the operating section 34. A scope connector 36a is provided at the other end of the universal cable 36. The scope connector 36a is connected to the control unit 14 and the light source unit 16.

The insertion section 32 includes an elongated insertion body 42, and a rotation unit 44 to be able to be attached to and detached from an outer periphery of the insertion body 42 and rotatable around a central axis C, which will be described later, of the insertion body 42. The rotation unit 44, which is rotatable around the central axis C, can be attached to and detached from an external side of the insertion body 42. The rotative force transmission unit 22, capable of transmitting a rotative force to the rotation unit 44 on a rotation gear 172, which will be described later, around a longitudinal axis L different from the central axis C, can be inserted into the insertion body 42 from an outside to an inside thereof, and can be detached from the insertion body 42 from the inside to the outside thereof.

The insertion body 42 includes, in the order from a distal end to a proximal end thereof, the distal-end rigid portion 52, an active bending portion 54, a passive bending portion 56 which passively bends when an external force is applied thereto, a first flexible tube 58, and a second flexible tube 60. The central axis C of the insertion section 32 is defined by the distal end (distal end of the distal-end rigid portion 52) and the proximal end (proximal end of the second flexible tube 60) of the insertion body 42.

The active bending portion 54 and the passive bending portion 56 are connected via a bending tube connector 62. The passive bending portion 56 and the first flexible tube 58 are connected via a relay connector 64. The first flexible tube 58 and the second flexible tube 60 are connected via a flexible tube connector 66. An anti-break member 68 is provided between the second flexible tube 60 and the operating section 34. That is, the insertion body 42 includes the bending tube connector 62, the relay connector 64, and the flexible tube connector 66, in addition to the distal-end rigid portion 52, the active bending portion 54, the passive bending portion 56, the first flexible tube 58, and the second flexible tube 60.

Distal ends of a variety of types of extension members 12a, such as an observation optical system, an illumination optical system, and a treatment tool channel, extending to the interior of the endoscope 12, are fixed to the distal-end rigid portion 52 shown in FIG. 1. The extension members 12a of the observation optical system and the illumination optical system are connected to the connector 36a through the interior of the insertion body 42, the interior of the operating section 34, and the interior of the universal cable 36. The extension member 12a of the treatment tool channel, i.e., the channel tube is connected to the operating section 34 through the interior of the insertion body 42.

FIG. 3 illustrates a side surface on the opposite side of the operating section 34 shown in FIG. 1. As shown in FIG. 3, the operating section 34 includes a treatment tool insertion opening 72, to which a proximal end of the extension member 12a of the treatment tool channel is connected. Accordingly, a treatment tool inserted from the treatment tool insertion opening 72 protrudes from the distal end of the distal-end rigid portion 52 through the extension member 12a, i.e., the treatment tool channel.

As will be described later, the operating section 34 includes an attachment portion 192 which is arranged in parallel to the treatment tool insertion opening 72 and to and from which the driving source 24 can be attached and detached.

As shown in FIG. 3, a bending operation knob 74 is provided on an outer surface of the operating section 34 as a bending operation input part to which a bending operation of the active bending portion 54 is input. In the interior of the operating section 34, a not-illustrated proximal end of a bending wire for bending the active bending portion 54, is connected to the bending operation knob 74. The bending wire extends along the central axis C to the interior of the insertion body 42 (insertion section 32), and a distal end of the bending wire is connected to a distal end of the active bending portion 54. When a bending operation is performed through the bending operation knob 74, the bending wire is towed and the active bending portion 54 is bent. The passive bending portion 56 is passively bent when an external force is applied thereto directly or indirectly via the passive bending portion 54. When an external force in a direction perpendicular to the central axis C is applied to the passive bending portion 56, for example, the passive bending portion 56 is bent. Furthermore, when an external force in a direction perpendicular to the central axis C is applied to the active bending portion 54, which has been bent, the external force is also applied to the passive bending portion 56 via the active bending portion 54, and the passive bending portion 56 is bent.

A variety of switches 76, such as air/water supply switches and suction switches, are provided in the operating section 34. Additionally, a rotating operation input switch 78, via which a signal is output for relatively rotating the rotation unit 44 around the central axis C of the insertion body 42 to the control unit 14, is provided in the operating section 34. The rotating operation input switch 78 outputs a signal that causes the rotation unit 44 to rotate in a first direction when the rotating operation input switch 78 is inclined by pressing the position indicated by the reference numeral 78a, and causes the rotation unit 44 to rotate in a second direction opposite to the first direction when the rotating operation input switch 78 is inclined by pressing the position indicated by the reference numeral 78b to the control unit 14.

The rotation unit 44 on the outer periphery of the insertion body 42 includes: a tube body 82 extending along the central axis C; a fin 84 extending in a spiral manner around the central axis C over an outer peripheral part of the tube body 82; a tube distal-end portion 86 in a cannular shape provided at the distal end of the tube body 82; and a tube proximal end portion 88 in a cannular shape provided at a proximal end of the tube body 82.

Figure 4:
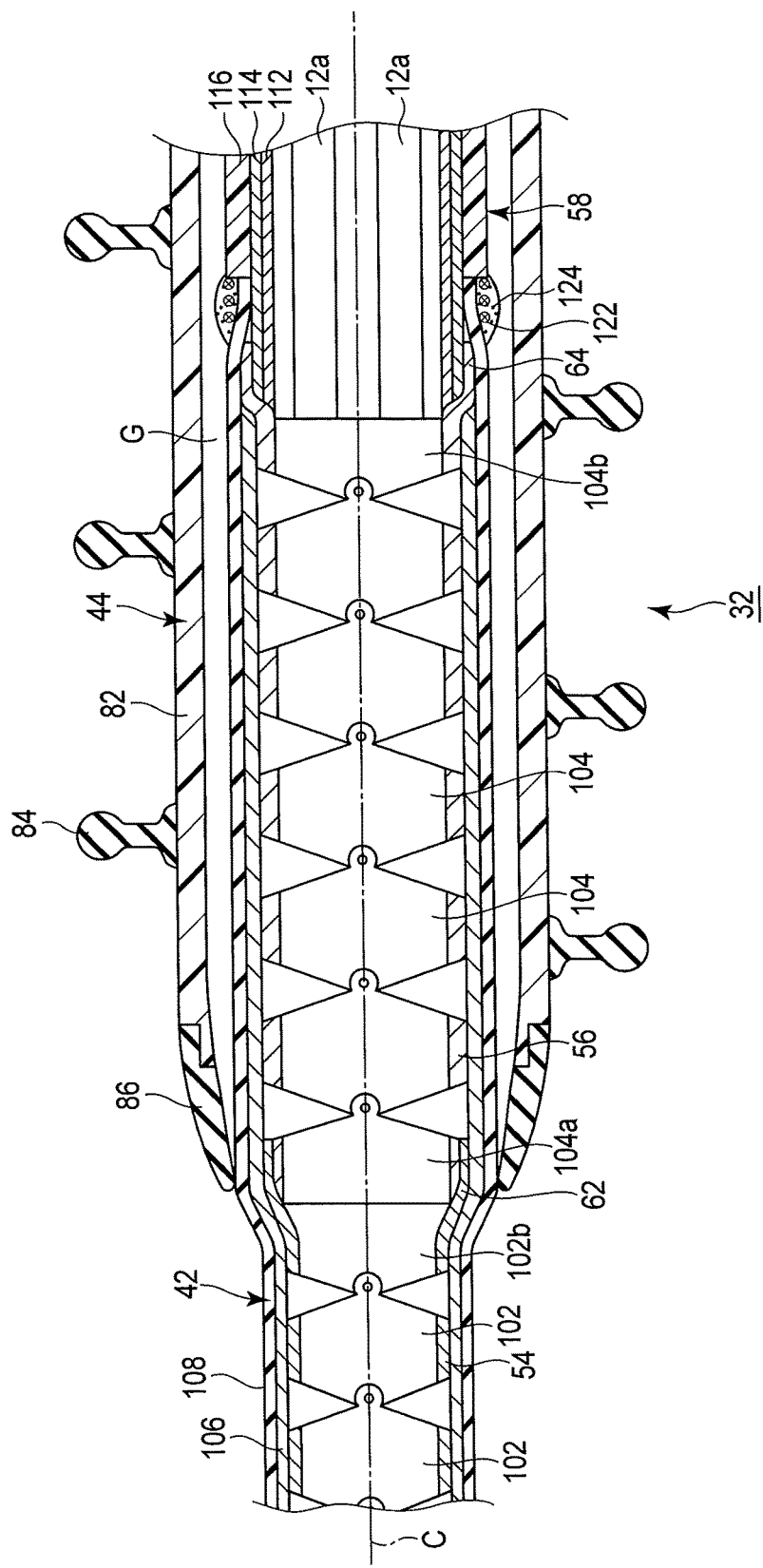
FIG. 4 is a schematic vertical sectional view illustrating a part of an active bending portion, a passive bending portion, and a part of a first flexible tube included in the insertion section of the endoscope of the endoscope system according to the embodiment.

FIG. 4 illustrates a configuration of the insertion body 42 and the rotation unit 44 in the vicinity of the passive bending portion 56. FIG. 5A to 6B illustrate a configuration of the insertion body 42 and the rotation unit 44 in the vicinity of the flexible tube connector 66.

As shown in FIG. 4, the active bending portion 54 includes a plurality of first joint rings 102 formed of metal. Each of the first joint rings 102 is rotatably coupled to the adjacent first joint ring 102. A distal end of the bending wire, not shown, is fixed to the first joint ring, not shown, positioned closest to the distal end side. When the bending wire is towed, the first joint ring 102 is rotationally moved around the first joint ring 102 to which the first joint ring 102 is adjacent, and the active bending portion 54 is bent.

The passive bending portion 56 includes a plurality of second joint rings 104 formed of metal. Each of the second joint rings 104 is rotationally coupled to the adjacent second joint ring 104. It is to be noted that a wire guide supporting the bending wire is not provided in each of the second joint rings 104. Accordingly, when an external force is applied in a direction perpendicular to the central axis C, the second joint ring 104 rotationally moves with respect to the adjacent second joint ring 104, and the passive bending portion 56 is bent.

The first joint ring 102b positioned closest to the proximal end side is fixed to the second joint ring 104a positioned closest to the distal end side so as to fit therein. Since the first joint ring 102b and the second joint ring 104a are fixed, the bending tube connector 62 is formed between the active bending portion 54 and the passive bending portion 56. Since the first joint ring 102b and the second joint ring 104a are fixed, a thickness of a metal part of the bending tube connector 62 formed by the first joint ring 102b and the second joint ring 104a becomes larger. Accordingly, the bending tube connector 62 becomes less flexible than the active bending portion 54 and the active bending portion 56, and will not be bent by an external force applied in a direction perpendicular to the central axis C.

An outer periphery of the first joint ring 102 and the second joint ring 104 are covered with a metal mesh tube (braid) 106. An outer periphery of the mesh tube 106 is covered with a sheath 108. The bending portion sheath 108 is formed of fluororubber, for example.

As shown in FIG. 4, the first flexible tube 58 includes a first helical tube (first flex) 112 formed of metal. An outer periphery of the first helical tube 112 is covered with a first mesh tube (first braid) 114 formed of metal. An outer periphery of the first mesh tube 114 is covered with a first sheath 116. The first sheath 116 is formed of a material that is less flexible than the sheath 108 of the active bending portion 54 and the passive bending portion 56, such as a mixed resin material of polyurethane and polyester. The bending properties of the first helical tube 112 when an external force is applied deteriorate, compared to a coupled body of the first joint rings 102 and a coupled body of the second joint rings 104. Accordingly, the first flexible tube 58 becomes less flexible than the active bending portion 54 and the passive bending portion 56. The first flexible tube 58 is provided so as to have flexibility that is high enough to be bent by an external force applied in the direction perpendicular to the central axis C.

The second joint ring 104b positioned closest to the proximal end side is fixed to the first helical tube 112 and the first mesh tube 114 so as to fit therein. Since the second joint ring 104b and the first helical tube 112 and the first mesh tube 114 are fixed, the relay connector 64 is formed between the passive bending portion 56 and the first flexible tube 58. Since the second joint 104b and the first helical tube 112 and the first mesh tube 114 are fixed, a thickness of a metal part of the relay connector 64 formed by the second joint ring 104b, the first helical tube 112, and the first mesh tube 114 becomes large. Accordingly, the relay connector 64 becomes less flexible than the passive bending portion 56 and the first flexible tube 58, and will not be bent by an external force applied in a direction perpendicular to the central axis C.

A proximal end of the bending portion sheath 108 and a distal end of the first sheath 116 are positioned at the relay connector 64. A thread 122 is wound around the first sheath 116 and the bending portion sheath 108 in an area between the bending portion sheath 108 and the first sheath 116, which is also coated with an adhesive agent 124.

The extension member 12a is inserted through an interior space of each of the first joint ring 102, the bending tube connector 62, the second joint ring 104, the relay connector 64, and the first helical tube 112, although not all are shown.

Figure 6A:
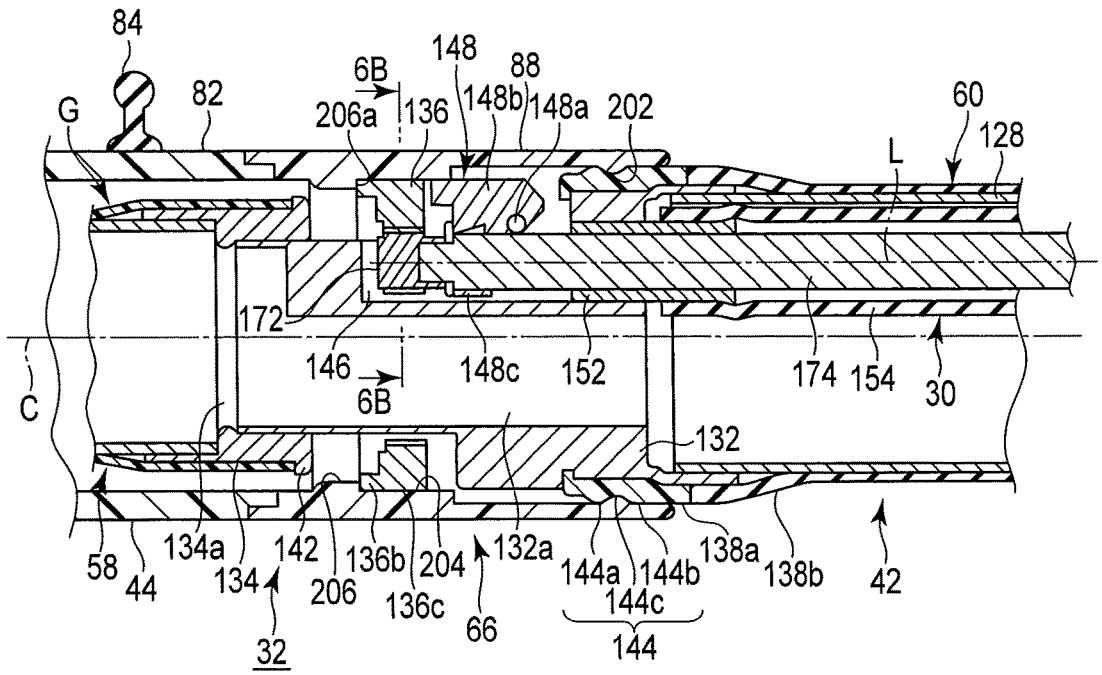
FIG. 6A is a schematic vertical sectional view illustrating a state in which a drive shaft of the rotative force transmission unit is introduced into the proximal end side of the insertion section from a flexible tube connector between the first flexible tube and the second flexible tube, and the rotation unit is arranged on an outer periphery of the insertion body such that the rotation unit is rotatable with respect to the insertion body, in the insertion section of the endoscope of the endoscope system according to the embodiment.

The second flexible tube 60 shown in FIGS. 5A, 5B, and 6A has a configuration that is similar to that of the first flexible tube 58. Accordingly, a detailed description of the second flexible tube 60 will be omitted, but the second flexible tube 60 is provided so as to have flexibility that is high enough to be bent by an external force applied in a direction perpendicular to the central axis C. It is to be noted that the cannular body indicated by the reference numeral 128 in FIGS. 5B and 6A represents a helical tube and a mesh tube provided on an outer periphery thereof. A second cover 138b, which will be described later, is used as a sheath. Accordingly, the first flexible tube 58 and the second flexible tube 60 have the same configuration.

As shown in FIGS. 5A to 6B, the flexible tube connector 66 between the first flexible tube 58 and the second flexible tube 60 includes a connecting mouth ring 132 formed of a metal material as a base, a distal-side mouth ring 134, a ring-shaped rotating body 136 including inner teeth (inner peripheral gear portion) 136a, and first and second covers 138a, 138b, each formed in a cylindrical shape. The connecting mouth ring 132 is arranged along the central axis C by the insertion body 42.

The distal-side mouth ring 134 is fixed to the proximal end of the first flexible tube 58. The distal-side mouth ring 134 includes a hollow space 134a, through which the extension member 12a (see FIG. 4), not shown in these drawings, is inserted. A flange 142 projecting outward in a radial direction is provided on an outer peripheral surface on the proximal end of the distal-side mouth ring 134. An annular portion 136b at a distal end of the rotating body 136 can be fit in the flange 142. That is, the proximal end of the distal-side mouth ring 134 can be fit in the annular portion 136b of the rotating body 136. Accordingly, the distal-side mouth ring 134 restricts movement of the rotating body 136 toward the distal end side of the insertion body 42, and can hold the rotating body 136 at the proximal end of the distal-side mouth ring 134.

The outer peripheral surface 136c of the rotating body 136 is formed in a shape other than a circle, such as an approximately regular octagon, so as to fit in a fitting surface 204, which will be described later, of the tube proximal end portion 88, for example, of the rotation unit 44.

A distal end of the connecting mouth ring 132 is fixed to the proximal end of the distal-side mouth ring 134. The connecting mouth ring 132 includes a hollow space 132a into which the extension member 12a (see FIG. 4), not shown in these drawings, is inserted, and which communicates with the hollow space 134a of the distal-side mouth ring 134.

The rotating body 136 is provided on an outer periphery of the connecting mouth ring 132 so as to be movable in the axis direction along the central axis C of the insertion body 42 and rotatable around the central axis C. A distal end of the second flexible tube 60 is fixed to a proximal end of the connecting mouth ring 132. Although not shown, the interior space of the first flexible tube 58, the hollow space 134a of the distal-side mouth ring 134, the hollow space 132a of the connecting mouth ring 132, and the interior space of the second flexible tube 60 communicate with one another and the extension member 12a is inserted therethrough.

An outer peripheral surface on the proximal end of the connecting mouth ring 132 is coated with a first cover 138a and a second cover 138b formed of a resin material, for example, and having insulating properties. The first cover 138a is provided on the outer periphery of the connecting mouth ring 132, while the second cover 138b is provided on an outer periphery of the second flexible tube 60. Preferably, the first cover 138a should be formed of a material harder than that of the second cover 138b. Further, a distal end of the second cover 138b is fixed to a distal end of the first cover 138a so as to butt thereagainst.

The first cover 138a includes an annular engaging portion 144 engaged with an annular engaging portion 202, which will be described later, of an inner peripheral surface of a tube proximal end portion 88 on an outer peripheral surface of the first cover 138a. In the present embodiment, an annular concave portion 144c is formed between a pair of annular convex portions 144a and 144b in the engaging portion 144 of the first cover 138a.

It is to be noted that the connecting mouth ring 132, the distal-side mouth ring 134, and the rotating body 136 are formed of a metal material, and are not easily bent with respect to the first flexible tube 58 and the second flexible tube 60. For example, even when an external force is applied to the flexible tube connector 66 by an inner wall such as the large intestine, the flexible tube connector 66 will not be bent.

Figure 6B:
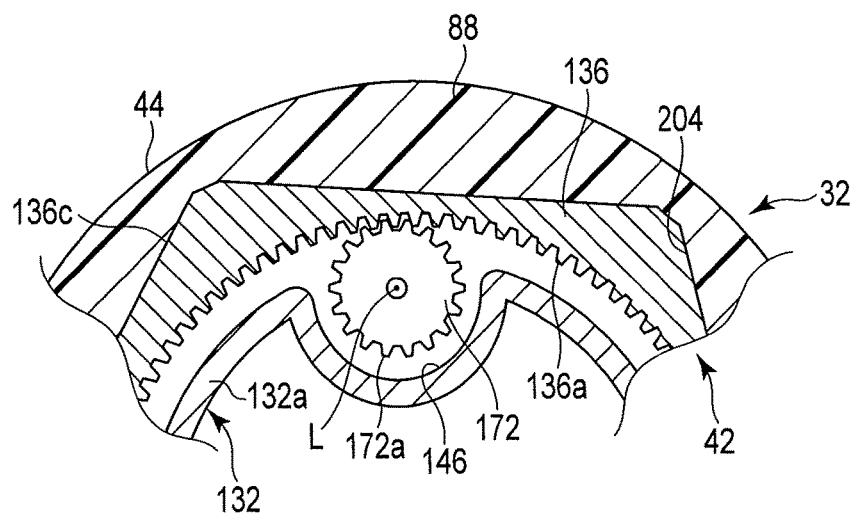
FIG. 6B is a schematic transverse sectional view of a position along the 6B-6B line of FIG. 6A.

As shown in FIGS. 5B and 6B, a gear arrangement hollow space 146 (opening end portion of the channel 30), in which a rotation gear (rotative force transmitting portion) 172, which will be described later, of the rotative force transmission unit 22 can be detachably arranged by a guide 148, which will be described later, is formed in the connecting mouth ring 132. The gear arrangement hollow space 146 is open to the outside of the connecting mouth ring 132. As shown in FIG. 6B, the gear arrangement hollow space 146 is formed so as to have a transverse section approximately in the shape of a letter U at that position. A part of the rotation gear 172 (upper area of FIG. 6B) is arranged in a position projecting from the gear arrangement hollow space 146, in a state in which the rotation gear 172 is arranged in the gear arrangement hollow space 146.

As shown in FIG. 5B, a guide 148 is pivotably supported by the connecting mouth ring 132 in a position close to (in the vicinity of) the gear arrangement hollow space 146. The guide 148 rotationally moves around a pivot shaft 148a in a direction orthogonal to the central axis C of the insertion body 42, with respect to the connecting mouth ring 132. The guide 148 includes a swing member 148b which rotationally moves around the pivot shaft 148a, and a cylindrical member (support portion) 148c formed integrally with the swing member 148b, and configured to guide and rotatably support the rotative force transmission unit 22. The swing member 148b of the guide 148 is formed so as to cover a part of the proximal end side of the gear arrangement hollow space 146. The guide 148 rotatably moves between the position shown in FIG. 5B and the position shown in FIG. 6A. When the guide 148 is in the position shown in FIG. 5B, the guide 148 comes into contact with a distal end of the first cover 138a, and thereby the maximum open position of the guide 148 is defined. When the guide 148 is in the position shown in FIG. 6A, the guide 148 is held by an inner peripheral surface of the tube proximal end portion 88, and thereby the closed position is defined. Since the cylindrical member 148c is formed integrally with the swing member 148b, the cylindrical member 148c rotationally moves as the swing member 148b of the guide 148 rotationally moves. An internal diameter of an inlet (most distal portion) of the cylindrical member 148c is greater than an outer diameter of a drive shaft 174, and is smaller than an outer diameter of a proximal end of the rotation gear 172. Accordingly, the cylindrical member 148c can support the drive shaft 174 of the rotative force transmission unit 22 so that the drive shaft 174 is rotatable around the longitudinal axis L.

Therefore, a ring (ring-shaped member) 150 is fixed to the inlet (distal-side position) of the cylindrical member 148c of the guide 148. That is, the guide 148 includes the ring 150. The ring 150 has an internal diameter equal to or greater than the maximum outer diameter of the drive shaft 174, and smaller than the outer diameter of the proximal end of the rotation gear 172. The ring 150 should preferably be an O ring formed of a resin material having heat-resistance and rub-resistance properties, such as a silicone material. The ring 150 is used as a restricting member configured to restrict movement of the rotation gear 172 to the proximal end side in the longitudinal axis L of each of the rotative force transmission unit 22, the guide 148, and a channel tube 154, which will be described later. The ring 150 does not need to be provided at the inlet of the cylindrical member 148c of the guide 148, and may preferably be provided on a side closer to a proximal end than a distal end of the cylindrical member 148c. Also, the internal diameter of the cylindrical member 148c of the guide 148 does not need to be constant, and the internal diameter of the inlet of the cylindrical member 148c may be greater than the outer diameter of the proximal end of the rotation gear 172.

In the connecting mouth ring 132, a cylindrical channel mouth ring 152 for the rotative force transmission unit 22 is fixed in a position that communicates with the gear arrangement hollow space 146. The channel mouth ring 152 is fixed watertight to the connecting mouth ring 132. A distal end of the channel tube 154 for the rotative force transmission unit 22 is fixed to an outer peripheral surface of the channel mouth ring 152. Accordingly, the drive shaft 174, which will be described later, of the rotative force transmission unit 22 can be inserted through the interior of the channel tube 154.

The channel tube 154 extends through the interior of the insertion body 42 along the longitudinal axis C toward the proximal end direction.

The channel tube 154 is fixed watertight to the channel mouth ring 152, and is arranged in parallel to the treatment tool channel tube, which is one of the extension members 12a.

As shown in FIG. 2A, the rotative force transmission unit 22 includes the rotation gear (rotative force transmitting portion) 172 formed in an approximately columnar shape and including an outer peripheral gear (external teeth) 172a on an outer periphery thereof, and the drive shaft 174. The rotation gear 172 has an outer diameter greater than an outer diameter of the drive shaft 174. The rotation gear 172 is fixed to a distal end of the drive shaft 174. The longitudinal axis L of the rotative force transmission unit 22 is defined by the rotation gear 172 and the drive shaft 174.

Figure 2B:
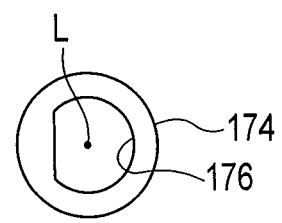
FIG. 2B is a schematic front view viewed from the arrow 2B of FIG. 2A.

The drive shaft 174 is formed in multiple layers by interlacing metal threads woven into a mesh cylindrical shape, or is formed of a multi-layer wire obtained by interlacing wire rods wound in a clockwise direction and a counterclockwise direction, for example, and has rotation followability and flexibility. As shown in FIG. 2B, the proximal end of the drive shaft 174 is formed in a circular shape, for example. A D-shaped concave portion 176 which fits a D-shaped rotation shaft 184 of the driving source 24, which will be described later, is formed at a proximal end of the drive shaft 174. Accordingly, the rotation of the rotation shaft 184 of the driving source 24 is transmitted to the drive shaft 174, and the rotation of the drive shaft 174 is transmitted to the rotation gear 172.

Figure 7A:
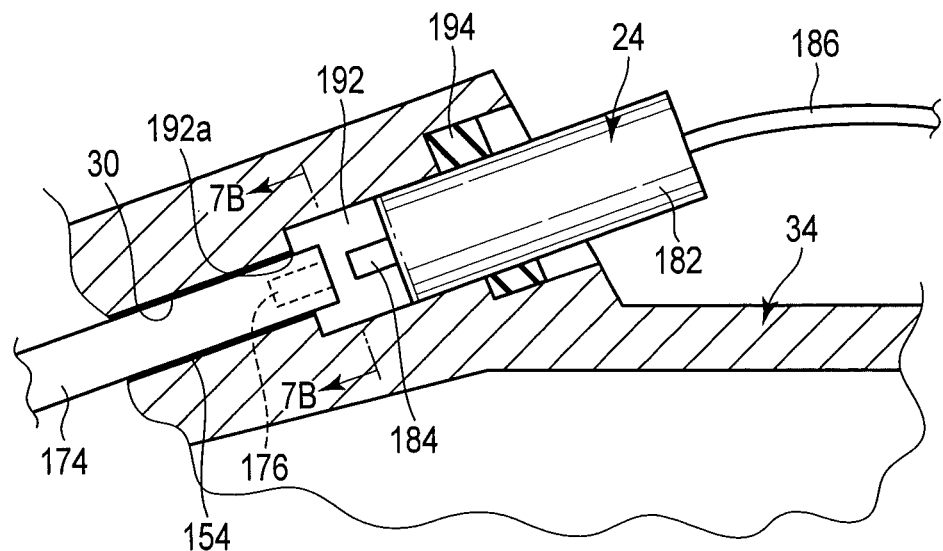
FIG. 7A is a schematic vertical sectional view illustrating a state in which a rotation axis of a driving source is being connected to a proximal end of the drive shaft through which the rotative force transmission unit is inserted via the insertion body and which protrudes toward the proximal end-side with respect to an outlet in the operating section of the endoscope of the endoscope system according to the embodiment.
Figure 7B:
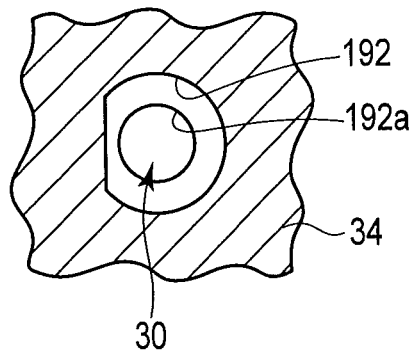
FIG. 7B is a transverse sectional view of a position along the arrow 7B-7B of FIG. 7A.

As shown in FIG. 7A, the driving source 24 includes a motor body 182, a rotation shaft 184, and a motor cable 186. A distal end of the motor cable 186 is detachably connected to the control unit 14. An outer shape of a transverse section of the rotation shaft 184 orthogonal to the rotation shaft 184 of the motor body 182 and an outer shape of a transverse section of the motor body 182 are formed approximately in the shape of a letter D, for example.

As shown in FIG. 7A, the operating section 34 includes an attachment portion 192, which defines the outlet 192a at the proximal end of the drive shaft 174 of the rotative force transmission unit 22 and to which the driving source 24, which will be described later, configured to transmit a rotative force to the proximal end of the drive shaft 174 is attached. A holding ring 194 configured to hold an outer periphery of the motor body 182 is provided in the attachment portion 192.

The channel tube 154 shown in FIGS. 5B and 6A is inserted through the outlet 192a of the attachment portion 192 through the interior of the insertion body 42 and the interior of the operating section 34. Accordingly, the proximal end of the channel tube 154 is open into the outlet 192a of the attachment portion 192.

As described above, in the flexible tube connector 66 and the second flexible tube 60 of the insertion body 42, the gear arrangement hollow space 146, the ring-shaped member 150, the cylindrical member 148c of the guide 148, the channel mouth ring 152, the channel tube 154, and the attachment portion 192 are defined in the order from the distal end to the proximal end, and thereby the channel 30 is formed as an insertion path through which the rotative force transmission unit 22 is inserted.

As shown in FIGS. 5B, 6A, and 6B, the rotation unit 44 is movable along the central axis C of the insertion body 42. In particular, the rotation unit 44 can be detachably attached to the insertion body 42 via the distal-end rigid portion 52.

The tube body 82 is formed of a resin material such as polyurethane. The tube body 82 includes a gap G between an outer peripheral surface of the bending portion sheath 108 shown in FIG. 4 and an outer peripheral surface of the first flexible tube 58 shown in FIG. 6A. That is, the tube body 82 is provided in a state in which a gap G is provided between the tube body 82 and the outer peripheral portion of the insertion body 42. This prevents friction between the insertion body 42 and the tube body 82 when the rotation unit 44 rotates with respect to the insertion body 42.

The tube distal-end portion 86 is formed of a material softer than that of the tube body 82, such as a rubber material. As shown in FIG. 4, the gap G between the rotation unit 44 and the bending portion sheath 108 becomes smaller in an inner peripheral part of the tube distal-end portion 85 than a part of the tube body 82 on the side of the inner peripheral direction.

The tube proximal end portion 88 of the rotation unit 44 may be integrally formed with the tube body 82, or may be separately formed. The tube proximal end portion 88 is formed in an annular shape, and includes a convex engaging portion 202, which can be engaged with the concave portion 144c of the engaging portion 144 of the flexible tube connector 66, on an inner peripheral surface on the proximal end side of the tube proximal end portion 88. An internal diameter of the engaging portion 202 is smaller than the maximum outer diameter of the convex portion 144a of the engaging portion 144 of the flexible tube connector 66, and is approximately equal to the minimum outer diameter of the concave portion 144c of the engaging portion 144 of the flexible tube connector 66. Accordingly, when the rotation unit 44 moves to the position shown in FIG. 6A from the position shown in FIG. 5B, the engaging portion 202 projecting inward in a radial direction of the tube proximal end portion 88 of the rotation unit 44 is elastically deformed together with the periphery thereof, extends over the convex portion 144a of the engaging portion 144 of the flexible tube connector 66, and is engaged with the convex portion 144c. While the engaging portions 144 and 202 are engaged with each other, the tube proximal end portion 88 exhibits a force capable of maintaining the engaged state.

The fitting surface 204, which has a shape that is the same as that of the outer peripheral surface 136c of the rotating body 136 and fits in the outer peripheral surface 136c of the rotating body 136, is formed on an inner periphery of the tube proximal end portion 88 on the side closer to the distal end than the engaging portion 202. An outer peripheral surface of the rotating body 136 and the fitting surface 204 shown in FIG. 6B are formed in an approximately octagonal shape, for example. The fitting surface 204 exists without a gap on the outer periphery in a position farther from the pivot shaft 148a of the guide 148, as shown in FIG. 6A. Accordingly, the fitting surface 204 fits in the outer peripheral surface 136c of the rotating body 136, and plays a role of regulating rotational movement of the guide 148.

In the tube proximal end portion 88, an annular convex portion 206 projecting inward in a radial direction is formed on the side closer to the distal end of the tube proximal end portion 88 than the fitting surface 204. The proximal end of the annular convex portion 206 includes a step (annular contact surface) 206a formed so as to contact with a distal end surface of the rotating body 136, and has a large internal diameter such that the annular convex portion 206 is movable along the central axis C with respect to the external side of the flange 142 of the distal-side mouth ring 134.

The fin 84 extending over the outer peripheral part of the tube body 82 is formed of a rubber material, for example.

The fin 84 is fixed to the tube body 82 by gluing or welding, for example. As shown in FIG. 1, the fin 84 extends in a clockwise spiral manner when viewed from the proximal end direction. The fin 84 of the rotation unit 44 contacts with the lumen wall when the insertion section 32 of the endoscope 1 is inserted into a lumen such as the interior of the small intestine or the large intestine. In this state, the rotating body 136 and the rotation unit 44 are rotated around the central axis C with respect to the insertion body 42. Thereby, an impelling force in a direction along the central axis C is applied to the insertion section 32.

Next, an action of the endoscope system 10 according to the present embodiment will be described. In the description given below, an assembly procedure for attaching the rotative force transmission unit 22 and the rotation unit 44 to the insertion body 42 and attaching the driving source 24 to the operating section 34 will be mainly discussed.

As shown in FIGS. 5A and 5B, the cylindrical member 148c of the guide 148 is tilted such that the longitudinal axis L of the guide 148 is inclined from the central axis C of the insertion body 42 (first position of the guide 148).

The drive shaft 174 of the rotative force transmission unit 22 shown in FIG. 2A is introduced from a proximal end thereof to the proximal end side of the insertion body 42 through the ring-shaped member 150 of the flexible tube connector 66, the cylindrical member 148c of the guide 148, the channel mouth ring 152, and the channel tube 154 shown in FIG. 5A. Since the proximal end of the rotation gear 172 has an outer diameter greater than an outer diameter of the drive shaft 174, movement of the rotation gear 172 is restricted by the ring-shaped member 150. In this case, the longitudinal axis L of the rotative force transmission unit 22 is inclined from the central axis C of the insertion body 42.

As shown in FIG. 7A, the proximal end of the drive shaft 174 is in the interior or in the vicinity of the attaching portion 192. In this state, the driving source 24 shown in FIG. 7A is attached to the attaching portion 192, and the rotation shaft 184 is made to fit in the D-shaped concave portion.

Further, the guide 148 in the position shown in FIGS. 5A and 5B is rotationally moved to the position shown in FIG. 6A (second position of the guide 148). Thereby, the rotation gear 172 is housed in the gear arrangement hollow space 146 by the cylindrical member 148c of the guide 148. At this time, the longitudinal axis L of the rotative force transmission unit 22 is parallel to the central axis C of the insertion body 42. In this state, the rotating body 136 in the position shown in FIGS. 5A and 5B is relatively moved toward the proximal end side of the insertion body 42 to the position shown in FIG. 6A. Thereby, as shown in FIG. 6B, inner teeth 136a of the rotating body 136 and an outer peripheral gear portion 172a of the rotation gear 172 are engaged with each other.

Therefore, the rotation unit 44 in the position shown in FIG. 5B is relatively moved toward the proximal end side of the insertion body 42 to the position shown in FIG. 6A. At this time, the engaging portion 202 of the rotation unit 44 comes into contact with the convex portion 144a of the first cover 138a via the external side of the rotating body 136, and the external side of the guide 148. By further moving the rotation unit 44 and elastically deforming the engaging portion 202 of the rotation unit 44 and the convex portion 144a of the first cover 138a, the engaging portion 202 of the rotation unit 44 is made to fit in the concave portion 144c of the first cover 138a.

At the same time, the rotating body 136 is rotationally moved as appropriate in the peripheral direction and aligned such that the outer peripheral surface 136c of the rotating body 136 and the fitting surface 204 of the tube proximal end portion 88 fit in each other. Further, the fitting surface 204 of the tube distal-end portion 88 is made to fit in the outer peripheral surface 136c of the rotating body 136.

At this time, depending on the position of the rotating body 136, the annular portion 136b at the distal end of the rotating body 136 comes into contact with the step 206a of the annular convex portion 206.

The insertion section 32 of the endoscope 12 becomes operational in this state. That is, the rotation unit 44 of the insertion section 32 becomes rotatable in the first direction and the second direction with respect to the central axis C.

For example, when the rotation unit 44 of the insertion section 32 is rotated in the first direction, the position indicated by the reference numeral 78a of a rotation operation input switch 78 shown in FIGS. 1 and 3 is pressed in a state in which the endoscope system 10 shown in FIG. 1 is activated. The press signal of the rotation operation input switch 78 is input to the control unit 14 via the universal cable 36 and the connector 36a. The control unit 14 rotates the rotation shaft 184 of the driving source 24 in the first direction via the motor cable 186 and the motor body 182. As the rotation shaft 184 is rotated in the first direction, the drive shaft 174 is rotated in the first direction. Since the drive shaft 174 is rotated in the first direction, the rotative force is transmitted to the rotation gear 172, and the rotation gear 172 is rotated in the first direction. Thereby, the rotating body 136 engaged with the rotation gear 172 is rotated in the first direction. As the rotating body 136 rotates in the first direction, the rotation unit 44 fitting in the rotating body 136 rotates in the first direction.

When the rotation unit 44 of the insertion section 32 is rotated in the second direction, the position indicated by the reference numeral 78b of the rotation operation input switch 78 is pressed in a state in which the endoscope system 10 shown in FIG. 1 is activated.

In the present embodiment, the fin 84 extends in a clockwise spiral manner when viewed from the proximal end direction. Accordingly, when the rotating body 136 and the rotation unit 44 rotate in a clockwise direction (first direction) when viewed from the proximal end direction, on the other hand, an impelling force toward the distal end direction is applied to the insertion section 32. Thereby, the insertion properties of the insertion section 32 in a lumen are improved. When the rotating body 136 and the rotation unit 44 are rotated in a counterclockwise direction (second direction) when viewed from the proximal end direction, an impelling force toward the proximal end direction is applied to the insertion section 32. Thereby, the extraction and removal properties of the insertion section 32 in a lumen are improved.

After the endoscope 12 is used, the endoscope 12 is cleaned, disinfected, sterilized, and then reused. A simple explanation of this procedure is as follows.

The procedure starts by removing the rotation shaft 184 of the driving source 24 from the concave portion 176 at the proximal end of the drive shaft 174.

The rotation unit 44 is moved to the distal end side of the insertion body 42, and the engaging portions 144 and 202 in the state shown in FIG. 6A are disengaged. Thus, engagement of the outer peripheral surface 136 of the rotating body 136 and the fitting surface 204 of the rotation unit 44 is released. That is, the rotation unit 44 is moved to the position shown in FIG. 5B with respect to the insertion body 42. After that, the rotating body 136 is moved so as to fit in the flange 142 of the distal-side mouth ring 134, and thereby the outer peripheral gear portion 172a of the rotation gear 172 and the inner teeth 136a of the rotating body 136 are disengaged from each other.

After that, the rotative force transmission unit 22 is removed from the channel 30 of the insertion body 42 by rotationally moving the guide 148 as shown in FIG. 5B, that is, by inclining the longitudinal axis L of the rotation gear 172 from the state parallel to the central axis C of the connecting mouth ring 132.

Thus, the interior of the channel 30 can be cleaned using a brush or the like, not shown, in a state in which the rotation unit 44 and the rotative force transmission unit 22 are removed from the insertion section 32.

The following effects are obtained according to the present embodiment.

The rotative force transmission unit 22 can be attached to the endoscope 12 from an intermediate point between the distal end and the proximal end of the insertion body 42. That is, according to the embodiment, it is possible to provide the insertion body 42 in which the rotative force transmission unit 22 can be arranged in an arrangement space (channel 30) from an intermediate point between the distal end and the proximal end of the insertion section 32, the insertion section (insertion apparatus) 32, and the rotation unit 44 and the rotative force transmission unit 22 which can be detachably attached to the insertion body 42. Since the rotation gear 172 is attached to the insertion body 42 after insertion of the drive shaft 174 of the rotative force transmission unit 22, it is possible to prevent the outer diameter of the insertion body 42, positioned closer to the proximal end than the position in which the rotation gear 172 is attached, from increasing due to the size of the rotation gear 172.

In the present embodiment, the guide 148 rotationally moves around the pivot shaft 148a, and the rotative force transmission unit 22 is detachably attached to the insertion body 42, by way of illustration. The rotative force transmission unit 22, however, may be configured not to be able to be removed from the insertion body 42, as long as the rotative force transmission unit 22 can be attached from an intermediate point between the distal end and the proximal end of the insertion body 42.

By arranging the ring-shaped member 150 in the guide 148, it is possible to regulate movement of the rotative force transmission unit 22 to the proximal end side. More specifically, movement of the rotation gear 172 to the proximal end side in the direction of the longitudinal axis L is prevented. Thereby, it is possible to prevent unintended disengagement of the outer peripheral gear portion 172a of the rotation gear 172 and the inner teeth 136a of the rotating body 136.

The rotation unit 44 according to the present embodiment can attach to and detach from the insertion body 42, and the rotative force transmission unit 22 and the driving source 24 can attach to and detach from the endoscope 12. Accordingly, cleaning and the like of the interior of the channel 30 can be easily performed. Further, cleaning and the like of the outer peripheral surface of the insertion body 42 can be easily performed.

When the rotation unit 44 is attached to and detached from the insertion body 42, the inner peripheral surface of the rotation unit 44 prevents the guide 148 from opening to the outside of the connecting mouth ring 132, fits in the rotating body 136, and regulates a range in which the rotating body 136 can move. That is, the rotating body 136 is held in a state in which the rotating body 136 fits in the flange 142 of the distal-side mouth ring 134 in the state shown in FIG. 5B, and the rotating body 136 is movable only between the distal end of the guide 148 and the step (contact surface) 206a in the state shown in FIG. 6A. Accordingly, when the rotative force transmission unit 22 is attached to and detached from the insertion body 42, it is possible to prevent the rotating body 136 from interfering, and when a rotative force from the rotative force transmission unit 22 is transmitted to the rotation unit 44, it is possible to easily transmit the rotative force.

When the rotative force transmission unit 22 is attached to and detached from the insertion body 42, since the swing member 148b and the cylindrical member 148c of the guide 148 rotationally move around the pivot shaft 148a, it is not necessary to add an excessive force that is large enough to bend the drive shaft 174 to an angle close to 90°, for example. By providing the guide 148 in the present embodiment, the rotative force transmission unit 22 can be easily attached to and detached from the channel 30 without adding an excessive force to the drive shaft 174 of the rotative force transmission unit 22.

In the present embodiment, the engaging portion 144 shown in FIGS. 5A to 6A and the engaging portion 202 shown in FIGS. 5B and 6A are engaged with each other, but this configuration may preferably be reversed. That is, the convex portion of the first cover 138a on the outer peripheral surface of the flexible tube connector 66 and the concave portion on the inner peripheral surface of the tube proximal end portion 88 may be engaged with each other.

In the present embodiment, the ring 150 is fixed to the inlet of the cylindrical member 148c of the guide 148, as shown in FIGS. 5A to 6A, by way of illustration. A similar effect can be obtained by fixing a ring (ring-shaped portion) 150a in the vicinity of a distal end portion of the drive shaft 174, as shown in FIG. 2C, instead of the ring 150. The ring 150a can be formed of a material that is similar to that of the ring 150.

Figure 8:
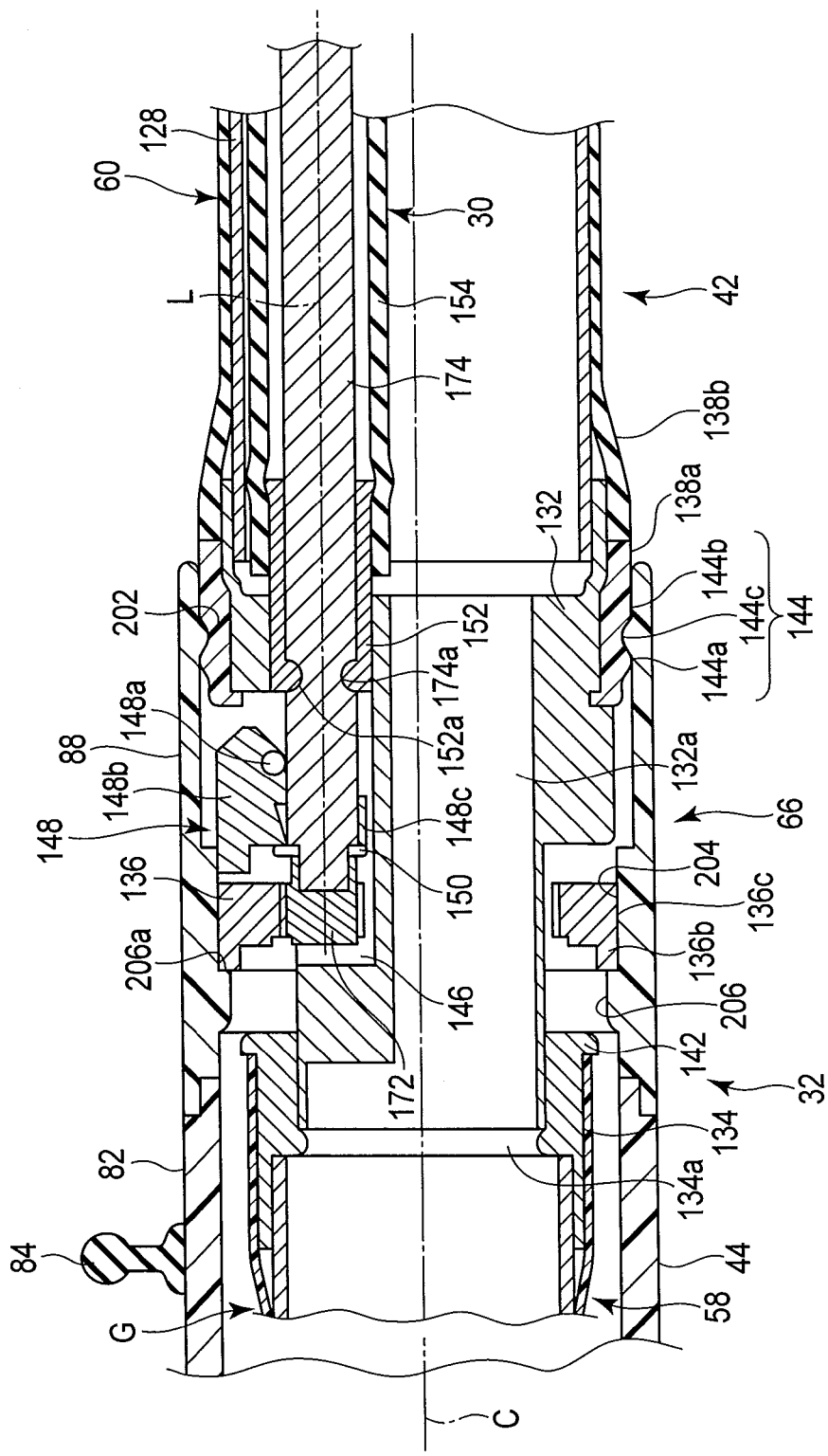
FIG. 8 is a schematic transverse sectional view illustrating a modification example of a restricting section configured to restrict movement of the drive shaft of the rotative force transmission unit to the proximal end-side of the insertion section, in the insertion section of the endoscope of the endoscope system according to the embodiment.

Furthermore, the structure shown in FIG. 8 may be adopted while using the ring 150 or instead of using the ring 150, or while using the ring 150a or instead of using the ring 150a. An annular convex portion (ring-shaped portion) 152a is formed on an inner peripheral surface of the distal end portion of the channel mouth ring 152, and a concave portion 174a, in which the annular convex portion 152a of the channel mouth ring 152 fits, is formed on an outer peripheral surface of the drive shaft 174. With these structures, an effect similar to that of when the rings 150 and 150a are used can be achieved.

The annular convex portion 152a of the channel mouth ring 152 and the concave portion 174a of the drive shaft 174 are exaggerated in FIG. 8; however, the annular convex portion 152a should only be large enough to be able to hold the outer peripheral surface of the drive shaft 174. That is, depending on the relationship between the internal diameter of the annular convex portion 152a and the outer diameter of the drive shaft 174, the convex portion 174a on the outer peripheral surface of the drive shaft 174 does not necessarily need to be provided.

A motor is used as the driving source 24 in the present embodiment by way of illustration, but the rotation shaft 184 may be manually rotated.

Further, the rotation unit 44 is attached to the insertion body 42 of the endoscope 12 in the above-described embodiment by way of illustration, but the apparatus to which the rotation unit 44 is attached is not limited to the endoscope 12. For example, it is also possible to adopt the structure of inserting the rotative force transmission unit 22 from an intermediate point of the insertion body 42 such as a surgical manipulator (insertion apparatus) to a proximal end side, and attaching the rotation unit 44 to an outer periphery of the insertion body 42.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Endoscopic insertion device for inserting into a body lumen, the insertion body comprising:
    a base having a distal portion, a proximal portion, a hollow space and an opening which communicates with the hollow space;
    a tube having a channel configured to receive a drive shaft, wherein a distal portion of the tube is connected to the base so as to communicate with the opening;
    a guide rotatably attached to the base about a pivot axis perpendicular to a central axis of the base, the central axis extending from the distal portion of the base to the proximal portion of the base, the guide being configured to hold a distal portion of the drive shaft inserted into the channel, the guide being rotatable about the pivot axis between a first position arranging the distal portion of the drive shaft in the hollow space and a second position arranging the distal portion of the drive shaft outside the hollow space; and
    an annular rotating body configured to rotate around the central axis in response to receiving rotation from the drive shaft when the drive shaft is supported by the guide arranged in the first position,
    wherein the guide inclines a longitudinal axis of the distal portion of the drive shaft with respect to the central axis of the base when the guide is in the second position.

2. The endoscopic insertion device according to claim 1, wherein, when the guide is arranged in the first position, the distal end of the drive shaft is arranged distally to the guide in a direction of the central axis.

3. The endoscopic insertion device according to claim 1, wherein the guide includes a pivot shaft on the pivot axis provided on the base, a swing member which is configured to swing around the pivot shaft, and a support portion provided on the swing member and configured to hold the distal portion of the drive shaft, and
    the longitudinal axis of the support portion of the guide is inclined from the central axis of the base when the guide is in the second position.

4. The endoscopic insertion device according to claim 3, wherein the support portion supports the drive shaft such that the distal portion of the drive shaft is rotatable around the longitudinal axis parallel to the central axis when the guide is in the first position.

5. The endoscopic insertion device according to claim 1, wherein the channel includes a restricting member configured to restrict a proximal movement of the drive shaft in a direction of the longitudinal axis.

6. The endoscopic insertion device according to claim 5, wherein the restricting member includes a ring-shaped member which permits rotation of the drive shaft around the longitudinal axis and prevents movement of the drive shaft in the direction of the longitudinal axis.

7. The endoscopic insertion device according to claim 1, wherein the opening is open into an outside of the base.

8. An endoscopic insertion apparatus comprising:
    the endoscopic insertion device according to claim 1; and
    the drive shaft, the drive shaft being configured to be inserted from an outside to an inside of the insertion body and removed from the inside to the outside of the insertion body, the drive shaft including a rotative force transmitting section at a distal end of the drive shaft, the rotative force transmitting section being capable of transmitting a rotative force to the annular rotating body.

9. The insertion apparatus according to claim 8, wherein the rotative force transmitting section includes an outer peripheral gear portion on an outer periphery of the drive shaft, and
    the annular rotating body includes an inner peripheral gear portion to which a rotative force from the outer peripheral gear portion is transmitted, on an inner periphery of the annular rotating body.

10. The insertion apparatus according to claim 9, further comprising a restricting member configured to restrict movement of the rotative force transmitting section towards a proximal side of the channel, the restricting member being provided on at least one of the drive shaft and the channel.

11. The insertion apparatus according to claim 10, wherein
    the drive shaft is able to be inserted through the channel to transmit the driving force from the proximal side to a distal side of the channel and to transmit the driving force to the rotative force transmitting section, and
    the restricting member of the channel includes a ring-shaped member which permits rotation of the drive shaft and prevents movement of the drive shaft in a direction of the central axis.

12. The insertion apparatus according to claim 11, wherein
    a proximal end of the rotative force transmitting section has an outer diameter greater than the maximum outer diameter of the drive shaft,
    the restricting member of the channel is in the guide, and
    the restricting member of the guide has an internal diameter equal to or greater than the maximum outer diameter of the drive shaft and an internal diameter smaller than an outer diameter of the proximal end of the rotative force transmitting section.

13. The insertion apparatus according to claim 8, further comprising a driving source which is able to be attached to and detached from a proximal portion of the tube to rotate the drive shaft.

14. The endoscopic insertion device according to claim 1, further comprising a rotation unit being rotatable according to rotation of the annular rotating body, the rotation unit being movable along the central axis with respect to the base between a position which is separated from the guide when the guide is in the second position, and a position which covers the guide when the guide is in the first position.

15. The endoscopic insertion device according to claim 14, wherein the rotation unit includes a spiral projection arranged on an exterior surface of the rotation unit.

16. The endoscopic insertion device according to claim 1, further comprising a bending portion which is bent, wherein the base, the annular rotating body and the channel are provided on a proximal side of a proximal end of the bending portion the direction of the central axis.

17. The endoscopic insertion device according to claim 1, wherein:

the annular rotating body is provided on an outer periphery of the base to be movable in a central axis direction of the base between a distal position and a proximal position, the annular rotating body is in the distal position when the drive shaft is supported by the guide in the second position; and the annular rotation body is configured to rotate around the central axis in response to receiving rotation from the drive shaft when the drive shaft is supported by the guide in the first position, the guide is in the first position, and the annular rotating body is in the proximal position.

* * * * *